US007153885B2

(12) United States Patent
Duran et al.

(10) Patent No.: US 7,153,885 B2
(45) Date of Patent: Dec. 26, 2006

(54) STOLONOXIDES

(75) Inventors: Rosario Duran, Cádiz (ES); Eva Zubia, Cádiz (ES); Maria J. Ortega, Cádiz (ES); Javier Salva, Cádiz (ES); Jose Luis Fernandez Puentes, Leon (ES); Dolores Garcia Gravalos, Tres Cantos (ES); Santiago Naranjo Lozano, Madrid (ES)

(73) Assignee: Universidad de Cadiz, Puerto Real (ES)

( * ) Notice: Subject to any disclaimer, the term of this patent is extended or adjusted under 35 U.S.C. 154(b) by 408 days.

(21) Appl. No.: 10/275,377

(22) PCT Filed: May 4, 2001

(86) PCT No.: PCT/GB01/01984

§ 371 (c)(1),
(2), (4) Date: Apr. 8, 2003

(87) PCT Pub. No.: WO01/83477

PCT Pub. Date: Nov. 8, 2001

(65) Prior Publication Data
US 2003/0166710 A1 Sep. 4, 2003

(30) Foreign Application Priority Data
May 4, 2000 (GB) .................................. 0010799.5

(51) Int. Cl.
A61K 31/335 (2006.01)
C07D 407/04 (2006.01)
(52) U.S. Cl. ........................................ 514/452; 549/414
(58) Field of Classification Search ................ 514/452; 549/414
See application file for complete search history.

(56) References Cited

OTHER PUBLICATIONS

Fontana et al., Tetrahedron Letters, vol. 41, (2000), pp. 429-432.*
Duran et al., Tetrahedron Letters, vol. 56, (2000), pp. 6031-6037.*
Davies-Coleman et al., J. Nat. Prod. vol. 63m (2000), pp. 1411-1413, XP-001007422.*
Cited in International Search report.*
Alali, Feras Q. et al., "Annonaceous Acetogenins: Recent Progress", *Journal of Natural Products*, vol. 62, No. 3, pp. 504-540 (1999).
Bergeron, Raymond J. et al., "Antineoplastic and Antiherpetic Activity of Spermidine Catecholamide Iron Chelators", *Biochemical and Biophysical Research Communications*, vol. 121, No. 3, pp. 848-854 (1984).
Davies-Coleman, Michael T. et al., "Stolonic Acids A and B, New Cytotoxic Cyclic Peroxides from an Indian Ocean Ascidian *Stolonica species*", *Journal of Natural Products*, vol. 63, No. 10, pp. 1411-1413 (2000).
Duran, Rosario et al., "Minor Metabolites from the Ascidian *Stolonica socialis* and Cytotoxicity of Stolonoxides", *Tetrahedron*, vol. 56, No. 33, pp. 6031-6037 (2000).
Duran, Rosario et al., "Novel Alkaloids from the Red Ascidian *Botryllus leachi*", *Tetrahedron*, vol. 55, No. 46, pp. 13225-13231 (1999).
Faulkner, D. John, "Marine Natural Products", *Natural Product Reports*, vol. 17, No. 1, pp. 7-55 (2000).
Fontana, Angelo et al., "Structure and Absolute Stereochemistry of Stononoxide A, a Novel Cyclic Peroxide from the Marine Tunicate *Stolonica socialis*", *Tetrahedron Letters*, vol. 41, pp. 429-432 (2000).
Gerwick, William H. "Epoxy Allylic Carbocations as Conceptual Intermediates in the Biogenesis of Diverse Marine Oxylipins", *Lipids*, vol. 31, No. 12, pp. 1215-1231 (1996).
Schroeder, Alan C. et al., "Synthesis and Biological Effects of Acyclic Pyrimidine Nucleoside Analogues", *Journal of Medicinal Chemistry*, vol. 24, No. 9, pp. 1078-1083 (1981).
Capon et al., "Trunculins A and B, Norsesterterpene Cyclic Peroxides from a Marine Sponge, *Latrunculia brevis*", *J. Org. Chem.*, 52:339-342 (1987).
Casteel, "Peroxy natural products", *Nat. Prod. Rep.*, 16:55-73 (1999).
Esposti et al., "Natural substances (acetogenins) from the family Annonaceae are powerful inhibitors of mitochondrial NADH dehydrogenase (Complex I)", *Biochem. J.*, 301:161-167 (1994).
He, et al., "Norsesterterpene Peroxides from the Sponge *Latrunculia* sp.", *J. Org. Chem.*, 56:2112-2115 (1991).
Oberlies et al., "Tumor cell growth inhibition by several Annonaceous acetogenins in an in vitro disk diffusion assay", *Cancer Letters*, 96:55-62 (1995).

* cited by examiner

*Primary Examiner*—Taofiq Solola
(74) *Attorney, Agent, or Firm*—Fish & Richardson P.C.

(57) ABSTRACT

Naturally occurring stolonoxide compounds, and derivatives thereof, have antitumor activity. Typical compounds are of the formula (I) or a derivative thereof (I)

$HOOC-H_2C$—[tetrahydrofuran with O-O]—[tetrahydrofuran]—$(CH_2)_6-(CH=CH)_2-(CH_2)_2-CH=CH_2$.

4 Claims, No Drawings

STOLONOXIDES

CROSS REFERENCE TO RELATED APPLICATIONS

This application is the National Stage of International Application No. PCT/GB01/01984, filed on May 4, 2001, which claims the benefit of Great Britain Application No. 0010799.5, filed on May 4, 2000.

The present invention relates to stolonoxides, including stolonoxide minor metabolites from the ascidian *Stolonica socialis* and derivatives thereof, and further relates to the cytotoxicity of stolonoxides.

BACKGROUND OF THE INVENTION

Marine ascidians continue to focus interest of both marine chemical and biomedical research. The chemistry of ascidians is dominated by amino acid derived compounds either peptides or alkaloids. However the non nitrogenous metabolites from ascidians, although considerably minor in number, are by no means less important, see Faulkner, D. J. *Nat. Prod. Rep.* 2000, 17, 7–55, and references cited therein. Among these non nitrogenous metabolites oxylipins, metabolites derived by biooxidation of fatty acids, are rarely encountered, see Gerwick, W. H. *Lipids* 1996, 31, 1215–1231.

The isolation of stolonoxide A, a novel cyclic peroxide isolated as its methyl ester from a sample collected from Tarifa Island (Cádiz, Spain) *Stolonica socialis*, has been reported, see Fontana, A; González, M. C.; Gavagnin, M.; Templado, J.; Cimino, G. *Tetrahedron Lett.* 2000, 41, 429-4-32.

SUMMARY OF INVENTION

According to the present invention, we provide pharmaceutical compositions of stolonoxide compounds. We also provide new stolonoxide compounds, including derivatives of naturally occuring compounds.

In one aspect, we provide pharmaceutical compositions of stolonoxide compounds of the formula:

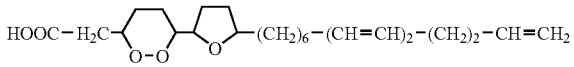

and derivatives thereof.

The compounds include natural isolates and compounds synthesised therefrom, and have cytotoxic activity against tumour cell lines.

Thus, the present invention provides a method of treating any mammal, notably a human, affected by cancer which comprises administering to the affected individual a therapeutically effective amount of a compound of the invention, or a pharmaceutical composition thereof.

The present invention also relates to pharmaceutical preparations including a pharmaceutically acceptable carrier and which contain as an active ingredient a compound or compounds of the invention. The invention extends to the processes for the preparation of the pharmaceutical compositions. Certain of the compounds can be readily isolated as mixtures, and such mixtures may be used in the compositions.

The present invention also extends to the compounds of the invention for use in a method of treatment, and to the use of the compounds in the preparation of a composition for treatment of cancer.

We further provide new stolonoxide compounds and derivatives, with the exception of the known methyl ester of stolonoxide A of formula:

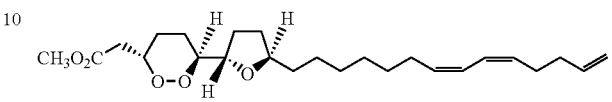

PREFERRED EMBODIMENTS

Preferred stolonoxides of this invention are stolonoxides A, B, C and D of the formulae:

(1)

(2)

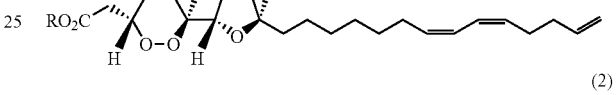

(3)

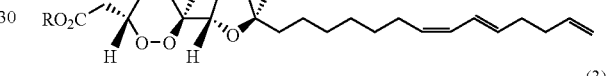

(4)

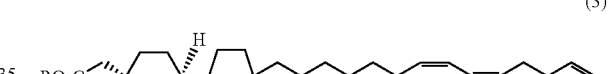

where R is H for the parent stolonoxide compound. Derivatives of the stolonoxides of this invention include those compounds formed by derivatisation of the carboxylic acid, which ate thus compounds where R is not hydrogen.

Examples of derivatives which form part of this invention include salts, especially alkali metal salts such as the sodium salt; esters, especially optionally substituted aliphatic or aryl esters such as $C_1$–$C_6$ or higher alkyl esters, cycloalkyl esters, alkenyl esters, alkynyl esters, aryl esters such as phenyl esters, aralkyl esters, aralkenyl esters, aralkynyl esters, all of which may be optionally substituted with alkyl, alkoxy, alkylthio, halogen, haloalkyl, carboxyl, hydroxy, hydroxyalkyl, aryl or aminoalkyl groups, and where the aryl groups may be heterocyclic; or amides, especially simple amides or N-substituted amides.

Suitable halogen substituents in the compounds of the present invention include F, Cl, Br and I.

Alkyl groups preferably have from 1 to 12 carbon atoms, more preferably 1 to 8 carbon atoms, still more preferably 1 to 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to 12 carbon atoms, more preferably 2 to 8 carbon atoms, still more prefereably 2 to 6 carbon atoms, even more prefereably 2, 3 or 4 carbon atoms. The terms alkenyl and alkynyl as used herein refere to both cyclic and noncyclic groups, although straight or branched noncyclic groups are generally more preferred.

Preferred alkoxy groups in the compounds of the present invention include groups having one or more oxygen linkages and from 1 to 12 carbon atoms, more preferably from 1 to 8 carbon atoms, and still more preferably 1 to 6 carbon atoms, and most preferably 1, 2, 3 or 4 carbon atoms.

Preferred alkylthio groups in the compounds of the present invention have one or more thioether linkages and from 1 to about 12 carbon atoms, more prefereably from 1 to about 8 carbon atoms, and still more preferably 1 to about 6 carbon atoms. Alkylthio groups having 1, 2, 3 or 4 carbon atoms are particularly preferred.

Preferred aminoalkyl groups include those groups having one or more primary, secondary and/or tertiary amine groups, and from 1 to 12 carbon atoms, more preferably 1 to 8 carbon atoms, still more preferably 1 to 6 carbon atoms, even more preferably 1, 2, 3 or 4 carbon atoms. Secondary and tertiary amine groups are generally more preferred than primary amine moieties.

Preferred amido groups include primary, secondary or tertiary amido groups, and include secondary or tertiary amido groups having one or more alkyl groups.

Suitable heterocyclic groups in the compounds of the present invention preferably contain one, two or three heteroatoms selected from nitrogen, oxygen and sulphur atoms and include heteroaromatic groups such as, for example, coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol; and heteroalicyclic groups such as, for example, tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic arykl groups include phenyl including substituted phenyl, such as 2-substituted phenyl, 3-substituted phenyl, 2,3-substituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

References herein to substituted groups in the compounds of the present invention refer to the specified moiety that may be substituted at one or more available positions by one or more suitable groups, for example, halogen such as fluoro, chloro, bromo and iodide; cyano; hydroxyl; nitro; azido; alkanoyl such as a $C_1$–$C_6$ alkanoyl group such as acyl and the like; carboxamido; alkyl groups including those groups having 1 to 2 carbon atoms or from 1 to 6 carbon atoms and more preferably 1–3 carbon atoms; alkenyl and alkynyl groups including groups having one or more unsaturated linkages and from 2 to 12 carbon or from 2 to 6 carbon atoms; alkoxy groups having those having one or more oxygen linkages and from 1 to 12 carbon atoms or 1 to 6 carbon atoms; aryloxy such as phenoxy; alkylthio groups including those moieties having one or more thioether linkages and from 1 to 12 carbon atoms or from 1 to 6 carbo atoms; alkylsulfinyl groups including those moieties having one or more sulfinyl linkages and from 1 to 12 carbon atoms or from 1 to 6 carbon atoms; alkylsulfinyl groups including those moieties having one or more sulfonyl linkages and from 1 to 12 carbon atoms or from 1 to 6 carbon atoms; aminoalkyl groups such as groups having one or more N atoms and from 1 to 12 carbon atoms or from 1 to 6 carbon atoms; carbocyclic aryl having 6 or more carbons, particularly phenyl (for instance a substituted or unsubstituted biphenyl moiety); and aralkyl such as benzyl.

The sidechain in the compounds can be 10-α or 10-β. The $\Delta^{19,20}$ double bond in the compounds can be cis or trans.

Examples of derivatives include compounds of formula (1a), (2a), (3a) and (4a), where the suffix "a" indicates a sodium salt, and compounds of formula (1b), (2b), (3b) and (4b) where the suffix "b" indicates a methyl ester. The compounds 2, 2a, 2b, 3a, and 4a are preferred compounds per se of this invention, while preferred compounds for antitumor activity include these compounds and compounds 1, 1a and 1b. The compounds of this invention can be in substantially pure form, and can be free from other cells or material from *Stolonica socialis*.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2–12 hs, with 2–6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time.

The identity of the other drug is not particularly limited, and suitable candidates included:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);
b) antimetabolite drugs such as 5-fluorouracil, cytarabine, gemcitabine, purine analogues such as pentostatin, methotrexate);
c) alkylating agents such as nitrogen mustards (such as cyclophosphamide or ifosphamide);
d) drugs which target DNA such as the antracycline drugs adriamycin, doxorubicin, pharmorubicin or epirubicin;
e) drugs which target topoisomerases such as etoposide;
f) hormones and hormone agonists or antagonists such as estrogents, antiestrogens (tamoxifen and related compounds) and androgens, flutamide, leuprorelin, goserelin, cyprotrone or octreotide;
g) drugs which target signal transduction in tumour cells including antibody derivatives such as herceptin;
h) alkylating drugs such as platinum drugs (cis-platin, carbonplatin, oxaliplatin, paraplatin) or nitrosoureas;
i) drugs potentially affecting metastasis of tumours such as matrix metalloproteinase inhibitors;
j) gene therapy and antisense agents;
k) antibody therapeutics;
l) other bioactive compounds of marine origin, notably the didemnins such as aplidine or the ecteinascidins such as Et-743;
m) steroid analogues, in particular dexamethasone;
n) anti-inflammatory drugs, in particular dexamethasone; and
o) anti-emetic drugs, in particular dexamethason.

Antitumour Assays

Cell Cultures. Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), $10^{-2}$ M sodium bicarbonate and 0.1 g/l penicillin-G+streptomycin sulfate.

A simple screening procedure has been carried out to determine and compare the antitumour activity of these compounds, using an adapted form of the method described by Bergeron et al (1984). The tumour cell line employed were P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-388 cell were seeded into 16 mm wells at $1\times10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximate $IC_{50}$ was determined by comparing the growth in wells with drug to the growth in wells contol.

A-549, HT-29 and MEL-28 were seeded into 16 mm wells at $2\times10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximate $IC_{50}$ was determined by comparing the growth in wells with drug to the growth in wells control.

Raymond J. Bergeron, Paul F. Cavanaugh, Jr., Steven J. Kline. Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121(3), 848–854.

Alan C. Schroeder, Robert G. Hughes, Jr. and Alexander Bloch. Effects of Acyclic Pyrimidine Nucleoside Analoges. *J. Med. Chem.* 1981, 24 1078–1083.

| Antitumoral in vitro data | | | | |
|---|---|---|---|---|
| | $IC_{50}$µg/ml | | | |
| Compound | P 388 | A 549 | HT 29 | MEL 28 |
| Mixture 1 and 2 (9:1) | 0.01 | 0.1 | 0.1 | 0.1 |
| Mixture 1a and 2a (6:4) | 0.05 | 0.1 | 0.1 | 0.1 |
| Mixture 3a and 4a (6:4) | 0.01 | 0.01 | 0.05 | 0.1 |
| Methyl ester (2b) | 0.5 | 0.1 | 0.1 | 0.5 |
| Methyl ester (1b) | 0.1 | 0.1 | 0.1 | Not tested |

EXAMPLES OF THE INVENTION

Bioassay guided isolation of the metabolites of the ascidian *Stolonica socialis* from Tarifa Island (Cádiz, Spain) led to a series of cyclic peroxides. A 9:1 mixture of stolonoxide A (1) and the new stolonoxide B (2), a 6:4 mixture of their corresponding sodium salts (1a, 2a), and a minor 6:4 mixture of the new stolonoxides C (3) and D (4) isolated as their sodium salts (3a) and (4a). Their structures were established by spectroscopic study of both the natural mixtures, whose constituents differ in the geometry of a double bond, and the corresponding methyl esters.

As a part of the research project carried aimed to examine the biomedical potential of new metabolites from ascidians of the southern coast of Spain, see (a) Durán, R.; Zubía, E.; Ortega, M. J.; Naranjo, S.; Salvá, J. *Tetrahedron* 1999, 55, 13225-1-13232; (b) Ortega, M. J.; Zubía, E.; Ocaña, J. M.; Naranjo, S.; Salvá, J. *Tetrahedron* accepted for publication, we collected specimens of the ascidian *Stolonica socialis* (Hartmeyer, 1903) belonging to the Styelidae Family. Specimens of *S. socialis* were collected by hand using SCUBA off Tarifa Island (Cádiz, Spain) and immediately frozen.

The frozen material was extracted with an acetone:methanol mixture (1:1). After evaporation of the solvent the aqueous residue was extracted with $Et_2O$ to yield a cytotoxic extract against the tumor cell lines of mouse lymphoma P-388, human lung carcinoma A-549 and human colon carcinoma HT-29 ($IC_{50}$=5 µg/mL). Column chromatography of the $Et_2O$ soluble material yielded six fractions of which fraction E was selected guided by the cytotoxicity against the tumor cell lines mentioned ($IC_{50}$=0.05 µg/mL). Further purification of this fraction using reversed phase HPLC allowed isolation of three pairs of compounds: a 9:1 mixture of stolonoxide A (1) and stolonoxide B (2), a 6:4 mixture of their corresponding sodium salts (1a and 2a), and a 6:4 mixture of the sodium salts of stolonoxide C and stolonoxide D (3 and 4). The individual components of each of these three pairs of compounds proved to be unseparable under all the HPLC conditions assayed and therefore it was necessary to derivatise the natural constituents.

Experimental Section

General. Optical rotations were measured on a Perkin-Elmer 241 polarimeter. IR and UV spectra were recorded on a Genesis Series FT IR Mattson and Phillips PU 8710 spectrophotometer, respectively. $^1$H and $^{13}$C NMR spectra were recorded at 400 and 100 MHz, respectively, on a Varian Unity 400 spectrometer using CDCl$_3$ as solvent. Proton chemical shifts were referenced to the residual CDCl$_3$ signal at δ 7.26 and $^{13}$C NMR spectra were referenced to the central peak of CDCl$_3$ at δ 77.0. $^1$H-$^1$H-COSY, LR COSY, HMQC and HMBC were performed using standard VARIAN pulse sequences. Assignments marked with an asterisk may be interchanged. Mass spectra were recorded on a VG Autospec spectrometer. Column chromatography was carried out using Merck Silica gel 60 (70–230 mesh). HPLC separations were performed on a LaChrom-Hitachi apparatus equipped with LiChrosorb RP-18 and LiChrosorb Si 60 columns using a differential refractometer. All solvents were spectral grade or were distilled from glass prior to use.

Collection, Extraction, and Isolation Procedures. Specimens of *Stoloilica socialis* (76 g dry weight) were collected by hand using SCUBA off Tarifa Island in May 1996 and immediately frozen. The frozen tissue was extracted with acetone-methanol (1:1) at room temperature. The filtered solution was evaporated under reduced pressure yielding an aqueous residue that was further extracted sequentially with Et$_2$O (4×450 mL) and n-BuOH (3×500 mL). The Et$_2$O extract was filtered and concentrated to yield 5.7 g of an orange cytotoxic oil (5.7 g) which was chromatographed on a SiO$_2$ column eluting with mixtures of increasing polarities from hexane to Et$_2$O and, subsequently, EOAc, CHCl$_3$/MeOH (1:1) and MeOH. Selected fractions were subjected to reversed phase HPLC separations on a preparative LiChrosorb RP-18 column eluting with MeOH/H$_2$O (9:1) to afford in order of elution: stolonoxide C and D sodium salts (3 and 4, 17 mg, 0.220% dry wt), stolonoxide A and B sodium salts (1a and 2a, 58 mg, 0.076% dry wt), stolonoxide A and B (1 and 2, 80 mg, 0.105% dry wt). Final purification was accomplished by HPLC on reversed phase mode using mixtures of MeOH/H$_2$O.

TABLE 1

$^1$H NMR data recorded in CDCl$_3$ for the natural metabolites from *Stolonica socialis*[a]

| | 1[b] | 2[b] | 1a | 2b | 3 | 4 |
|---|---|---|---|---|---|---|
| 2 | 2.49 (dd, 15.8, 7.2) | | 2.26 (m) | | 2.34 (m) | |
| | 2.44 (dd, 15.8, 5.3) | | | | | |
| 3 | 4.52 (m) | | 4.45 (m) | | 4.48 (m) | |
| 4 | 1.95 (m, Heq) | | 1.90 (m, Heq) | | 1.91 (m, Heq) | |
| | 1.60 (m, Hax) | | 1.49 (m, Hax) | | 1.52 (m, Hax) | |
| 5 | 1.73 (m) | | 1.60 (m) | | 1.65 (m) | |
| 6 | 4.07 (m) | | 4.00 (m) | | 4.02 (m) | |
| 7 | 3.87 (m) | | 3.79 (m) | | 3.82 (bd, 6.0) | |
| 8 | 1.95 (m) | | 1.92 (m) | | 1.95(m) | |
| | 1.77 (m) | | 1.66 (m) | | 1.70 (m) | |
| 9 | 2.00 (m) | | 1.97 (m) | | 1.97 (m) | |
| | 1.44 (m) | | 1.43 (m) | | 1.43 (m) | |
| 10 | 3.87 (m) | | 3.88 (m) | | 3.88 (m) | |
| 11 | 1.58 (m) | | 1.60 (m) | | 1.60 (m) | |
| | 1.33 (m) | | 1.32 (m) | | 1.34 (m) | |
| 12 | 1.30–1.20 (m) | | 1.30–1.20 (m) | | 1.30–1.20 (m) | |
| 13 | 1.30–1.20 (m) | | 1.30–1.20 (m) | | 1.30–1.20 (m) | |
| 14 | 1.30–1.20 (m) | | 1.30–1.20 (m) | | 1.30–1.20 (m) | |
| 15 | 1.30–1.20 (m) | | 1.30–1.20 (m) | | 1.30–1.20 (m) | |
| 16 | 2.15 (m) | | 2.14 (m) | | 2.15 (m) | |
| 17 | 5.44 (m) | 5.30 (m) | 5.44 (m) | 5.30 (m) | 5.44 (m) | 5.31 (dt, 10.9, 7.4) |
| 18 | 6.25 (m) | 5.96 (bt, 10.8) | 6.24 (m) | 5.94 (bt, 10.6) | 6.24 (m) | 5.93 (bt, 10.9) |
| 19 | 6.25 (m) | 6.30 (m) | 6.24 (m) | 6.31 (m) | 6.24 (m) | 6.31 (bdd, 15.2, 10.9) |
| 20 | 5.44 (m) | 5.65 (m) | 5.44 (m) | 5.65 (m) | 5.44 (m) | 5.65 (bdt, 15.2, 6.6) |
| 21 | 2.27 (bdd, 14.7, 7.5) | 2.17 (m) | 2.26 (m) | 2.17 (m) | 2.27 (bdd, 14.8, 7.5) | 2.18 (m) |
| 22 | 2.13 (m) | | 2.14 (m) | | 2.15 (m) | |
| 23 | 5.82 (ddt, 17.0, 10.2, 6.5) | | 5.82 (ddt, 16.9, 10.3, 6.5) | | 5.82 (ddt, 17.0, 10.2, 6.5) | |
| 24 | 5.03 (ddd, 17.0, 1.7, 1.6) | | 5.03 bd, 16.9) | | 5.03 (bd, 17.0) | |
| | 4.96 (bd, 10.2) | | 4.97 (bd, 10.3) | | 4.96 (bd, 10.2) | |

[a]Assignments were aided by COSY, LR COSY and HMQC experiments.
[b]Assignments were aided by an HMBC experiment.

TABLE 2

$^{13}$C NMR data recorded in CDCl$_3$ for the natural metabolites from *Stolonica socialis*[a]

| | 1[b] | 2[b] | 1a | 2b | 3 | 4 |
|---|---|---|---|---|---|---|
| 1 | 175.1 (s) | | 177.1 (s) | | 176.0 (s) | |
| 2 | 38.4 (t) | | 41.3 (t) | | 40.0 (t) | |
| 3 | 77.4 (d) | | 79.2 (d) | | 78.5 (d) | |
| 4 | 29.0 (t) | | 29.0 (t) | | 29.0 (t) | |
| 5 | 25.1 (t) | | 25.1 (t) | | 25.1 (t) | |
| 6 | 83.8 (d) | | 84.0 (d) | | 84.0 (d) | |
| 7 | 78.5 (d) | | 78.7 (d) | | 78.6 (d) | |
| 8 | 27.7 (t) | | 28.1 (t) | | 28.0 (t) | |
| 9 | 31.6 (t) | | 31.6 (t) | | 31.6 (t) | |

TABLE 2-continued

¹³C NMR data recorded in CDCl₃ for the natural metabolites from *Stolonica socialis*[a]

| 1[b] | 2[b] | 1a | 2b | 3 | 4 |
|---|---|---|---|---|---|
| 10 80.0 (d) | | 79.9 (d) | | 79.9 (d) | |
| 11 35.5 (t) | | 35.6 (t) | | 35.6 (t) | |
| 12 26.0 (t) | | 25.9 (t) | | 26.0 (t) | |
| 13 29.6 (t)[c] | | 29.7 (t)[c] | | 29.7 (t)[c] | |
| 14 29.5 (t)[c] | | 29.6 (t)[c] | | 29.6 (t)[c] | |
| 15 29.2 (t)[c] | | 29.3 (t)[c] | | 29.3 (t)[c] | |
| 16 27.4 (t) | 27.7 (t) | 27.5 (t) | 27.7 (t) | 27.5 (t) | 27.8 (t) |
| 17 132.4 | 130.4 | 132.3 | 130.4 | 132.4 | 130.4 |
| 18 123.4 | 128.4 | 123.5 | 128.5 | 123.5 | 128.5 |
| 19 124.0 | 126.0 | 124.0 | 126.0 | 124.0 | 126.1 |
| 20 130.8 | 133.4 | 130.8 | 133.5 | 130.8 | 133.5 |
| 21 26.8 (t) | 32.2 (t) | 26.9 (t) | 32.2 (t) | 26.9 (t) | 32.2 (t) |
| 22 33.7 (t) | | 33.7 (t) | | 33.7 (t) | |
| 23 138.2 (d) | | 138.2 (d) | | 138.2 (d) | |
| 24 114.7 (t) | | 114.8 (t) | | 114.8 (t) | |

[a]Assignments were aided by an HMQC experiment.
[b]Assignments were aided by an HMBC experiment.
[c]Values with the same superscript in the same column may be interchanged.

Stolonoxides A and B (1 and 2): amorphous powder; $[\alpha]^{D25}$ −62.90 (c 0.49, CHCl₃); IR (film) 3460, 1745, 1237, 1064 cm⁻¹; UV (MeOH) $\lambda_{max}$234 (ε=20400) nm; ¹H NMR (CDCl₃) see Table 1; ¹³C NMR (CDCl₃) see Table 2; EIMS (70 eV) m/z (rel. int.) 406 (18), 388 (7), 344 (5), 261 (10), 219 (5), 135 (15), 121 (23), 95 (50), 67 (100); HREIMS m/z 406.2734, $C_{24}H_{38}O_5$ requires m/z 406.2719.

Stolonoxides A and B sodium salts (1a and 2a): amorphous powder; $[\alpha]_D^{25}$ −76.8° (c 0.19, CHCl₃); IR (film) 1579, 1435, 1070 cm¹; UV (MeOH) $\lambda_{max}$ 234 (ε 19600) nm; ¹H NMR (CDCl₃) see Table 1; ¹³C NMR (CDCl₃) see Table 2; (−)LRESIMS m/z (rel. int.) 405 [M−Na]−(100), (+)LRESIMS m/z (rel. int.) 429 [M+H]⁺ (100), 451 [M+Na]⁺ (5); HREIMS m/z 406.2766, $C_{24}H_{38}O_5$ requires m/z 406.2719.

Stolonoxides C and D sodium salts (3a and 4a): amorphous powder; $[\alpha]_D^{25}$ +38.0° (c 0.2, CHCl₃); IR (film) 1584, 1440, 1057 cm⁻¹; UV (MeOH) $\lambda_{max}$ 234 (ε=22500) nm; ¹H NMR (CDCl₃) see Table 1; ¹³C NMR (CDCl₃) see Table 2; (−)LRESIMS m/z (rel. int.) 405 [M−Na]⁻ (100), (+)LRESIMS m/z (rel. int.) 429 [M+H]⁺ (100); HREIMS m/z 388.2639, $C_{24}H_{36}O_4$ requires m/z 388.2614.

Methylation of the mixture of stolonoxides A (1) and B (2): Excess of CH₂N₂ was added to a solution of the mixture of stolonoxide A (1) and B (2) (22 mg) in Et₂O (2 mL) at room temperature. After 1 h, the solvent was removed under reduced pressure and the reaction crude subjected to HPLC chromatography yielding stolonoxide A methyl ester (1b, 18 mg) and stolonoxide B methyl ester (2b, 2 mg).

Methylation of the mixtures 1a, 2a, and 3,4: Methylation of these mixtures was performed using the same procedure described above but the mixtures were previously acidified with a solution of 1N HCl.

Stolonoxide A methyl ester (1b): colorless oil; $[\alpha]_D^{25}$ −50.8° (c 0.39, CHCl₃); IR (film) 1745, 1640, 1200, 1060 cm⁻¹; UV (MeOH) $\lambda_{max}$235 (ε=22000) nm- ¹H NMR (CDCl₃) 6.25 (m, 2H, H-18 and H-19), 5.82 (ddt, J=16.9, 10.3, 6.6 Hz, 1H, H-23), 5.44 (m, 2H, H-17 and H-20), 5.03 (ddd, J=16.9, 1.7, 1.6 Hz, 1H, H-24), 4.97 (bd, J=10.3 Hz, 1H, H-24), 4.54 (dddd, J=11.1, 7.7, 5.9, 2.2 Hz, 1H, H-3), 4.06 (ddd, J=11.1, 5.4, 2.4 Hz, 1H, H-6), 3.87 (m, 2H, H-7 and H-10), 3.69 (s, 3H, CH₃O−), 2.47 (dd, J=15.6, 7.7 Hz, 1H, H-2), 2.36 (dd, J=15.6, 5.9 Hz, 1H, H-2), 2.28 (bdd, J=14.7, 7.4, 2H, H-21), 2.15 (m, 2H, H-16), 2.13 (m, 2H, H-22), 1.99 (m, 1H, H-9), 1.95 (m, 1H, H-8), 1.92 (m, 1H, H-4eq), 1.77 (m, 2H, H-5ax and H-8), 1.70 (m, 1H, H-5eq), 1.58 (m, 1H, H-11),1.54 (m, 1H, H-4ax), 1.42 (m, 1H, H-9), 1.34 (m, 1H, H-11), 1.33 (m, 1H, H-12), 1.30 (m, 6H, H-13, H-14 and H-15), 1.28 (in, 1H, H-12); ¹³C NMR (CDCl₃) 170.4 (s, C-1), 138.2 (d, C-23), 132.4 (d, C-17), 130.8 (d, C-20), 124.0 (d, C-19), 123.4 (d, C-18), 114.7 (t, C-24), 83.8 (d, C-6), 79.9 (d, C-10), 78.5 (d, C-7), 77.6 (d, C-3), 51.9 (q, CH₃O—), 38.4 (t, C-2), 35.6 (t, C-11), 33.7 (t, C-22), 31.7 (t, C-9), 29.6 (t, C-13)*, 29.5 (t, C-14)*, 29.2 (t, C-15)*, 29.1 (t, C-4), 27.7 (t, C-8), 27.5 (t, C-16), 26.8 (t, C-21), 26.0 (t, C-12), 25.2 (t, C-5); EIMS (70 eV) m/z (rel. int.) 420 (2), 402 (18), 261 (25), 219 (7), 159 (15), 143 (36), 135 (29), 121 (41), 67 (100); HREIMS m/z 420.2865, $C_{25}H_{40}O_5$ requires m/z 420.2876.

Stolonoxide B methyl ester (2b): colorless oil; $[\alpha]_D^{25}$−37.7° (c 0.26, CHCl₃); IR (film) 1745, 1200, 1090 cm⁻¹; UV (MeOH) $\lambda_{max}$ 233 (ε=19900) nm; ¹H NMR (CDCl₃) 6.32 (dd, J=15.1, 11.0 Hz, 1H, H-19), 5.94 (t, J=11.0 Hz, 1H, H-18), 5.82 (ddt, J=16.9, 10.3, 6.6 Hz, 1H, H-23), 5.65 (dt, J=15.1, 6.7 Hz, 1H, H-20), 5.31 (dt, J=11.0, 7.6 Hz, 1H, H-17), 5.03 (ddd, J=16.9, 1.6, 1.3 Hz, 1H, H-24), 4.97 (bd, J=10.3 Hz, 1H, H-24), 4.54 (dddd, J=11.2, 7.7, 6.0, 2.3 Hz, 1H, H-3),4.06 (ddd, J=11.0, 5.6, 2.6 Hz, 1H, H-6), 3.87 (m, 2H, H-7 and H-10), 3.69 (s, 3H, CH₃O—), 2.47 (dd, J=15.6, 7.7 Hz, 1H, H-2), 2.36 (dd, J=15.6, 6.0 Hz, 1H, H-2), 2.20 (m, 2H, H-21), 2.17 (m, 2H, H-22), 2.14 (m, 2H, H-16), 1.99 (m, 1H, H-9), 1.95 (m, 1H, H-8), 1.92 (m, 1H, H-4eq), 1.77 (m, 2H, H-5ax and H-8), 1.70 (m, 1H, H-5eq), 1.58 (m, 1H, H-11), 1.54 (m, 1H, H-4ax), 1.42 (m, 1H, H-9), 1.34 (m, 1H, H-11), 1.33 (m, 1H, H12), 1.30 (m, 6H, H-13, H-14 and H-15), 1.28 (m, 1H, H-12); ¹³C NMR (CDCl₃) 170.4 (s, C-1), 138.2 (d, C-23), 133.5 (d, C-20), 130.5 (d, C-17), 128.4 (d, C-18), 126.1 (d, C-19), 114.7 (t, C-24), 83.8 (d, C-6), 79.9 (d, C-₁₀), 78.5 (d, C-7), 77.6 (d, C-3), 51.2 (q, CH₃0-), 38.4 (t, C-2), 35.6 (t, C-11), 33.6 (t, C-22), 32.7 (t, C-9), 32.2 (t, C-21), 29.6 (t, C-13)*, 29.6 (t, C-14)*, 29.2 (t, C-15)*, 29.1 (t, C-4),27.7 (t, C-8), 27.7 (t, C16),26.0 (t, C-12), 25.2 (t, C-5); EIMS (70 eV) m/z (rel. int.) 420 (2), 402 (17), 261 (27), 219 (9), 159 (17), 143 (76), 121 (61), 67 (100); HREIMS m/z 420.2866, $C_{25}H_{40}O_5$ requires m/z 420.2876.

Stolonoxides C and D methyl esters (3a and 4a): colorless oil; $[\alpha]_D^{25}$ +41.7° (c 0.3, CHCl₃); IR (film) 1745,1200, 1060 cm⁻¹; UV (MeOH) $\lambda_{max}$ 234 (ε=19600) nm; ¹H NMR (CDCl₃) see Table 1; ¹³C NMR (CDCl₃) see Table 2; EIMS (70 eV) m/z (rel. int.) 420 (2), 402 (23), 261 (23), 219 (6), 159 (10), 143 (27), 121 (35), 67 (100); HREIMS m/z 420.2863, $C_{25}H_{40}O_5$ requires m/z 420.2876.

3a: ¹H NMR (CDCl₃) 6.25 (m, 2H, H-18 and H-19), 5.82 (ddt, J=17.0, 10.2, 6.6 Hz, 1H, H-23), 5.44 (m, 2H, H-17 and H-20), 5.03 (bd, J=17.0 Hz, 1H, H-24), 4.97 (bd, J=10.2 Hz, 1H, H-24), 4.54 (dddd, J=11.0, 7.7, 5.9, 2.2 Hz, 1H, H-3), 4.03 (ddd, J=10.9, 6.0, 2.1 Hz, 1H, H-6), 3.86 (m, 1H, H-10), 3.80 (q, J=6.0 Hz, 1H, H-7), 3.69 (s, 3H, CH₃O—), 2.47 (dd, J=15.6, 7.7 Hz, 1H, H-2), 2.37 (dd, J=15.7, 5.9 Hz, 1H, H-2), 2.28 (bdd, J=14.7, 7.4 Hz, 2H, H-21), 2.16 (m, 2H, H-16), 2.14 (m, 2H, H-22), 2.00 (m, 1H, H-8), 1.98 (m, 1H, H-9), 1.94 (m, 1H, H-5eq), 1.92 (m, 1H, H-4eq), 1.80 (m, 1H, H-8), 1.65 (m, 1H, H-5ax), 1.56 (m, 1H, H-11), 1.55 (m, 1H, H-4ax), 1.45 (m, 1H, H-9), 1.38 (m, 1H, H-12), 1.37 (m, 1H, H-11), 1.28 (m, 1H, H-12), 1.30–1.20 (m, 6H, H-13, H-14 and H-15); ¹³C NMR (CDCl₃) 170.4 (s, C-1), 138.2 (d, C-23), 132.4 (d, C-17), 130.9 (d, C-20), 124.0 (d, C-19), 123.5 (d, C-18), 114.8 (t, C-24), 83.7 (d, C-6), 79.9 (d, C-10), 78.5 (d, C-7), 77.8 (d, C-3), 51.9 (q, $CH_3O$—), 38.4 (t, C-2), 35.6 (t, C11), 33.7 (t, C-22), 31.6 (t, C-9), 29.6 (t, C-13)*, 29.5 (t, C-14)*, 29.2 (t, C-15)*, 28.9 (t, C-4), 28.0 (t, C-8), 27.5 (t, C-16), 26.9 (t, C-21), 26.1 (t, C-12), 25.7 (t, C-5).

4a: $^1$H NMR ($CDCl_3$) 6.32 (m, 1H, H-19), 5.94 (bt, J=10.9 Hz, 1H, H-18), 5.82 (ddt, J=17.0, 10.2, 6.6 Hz, 1H, H-23), 5.66 (dt, J=14.4, 6.4 Hz, 1H, H-20), 5.30 (dt, J=10.9, 7.3 Hz, 1H, H-17), 5.03 (bd, J=17.0 Hz, 1H, H-24), 4.97 (bd, J=10.2 Hz, 1H, H-24), 4.54 (dddd, J=11.0, 7.7, 5.8, 2.2 Hz, 1H, H-3), 4.03 (ddd, J=10.9, 6.0, 2.1 Hz, 1H, H-6), 3.86 (m, 1H, H-10), 3.80 (q, J=6.0 Hz, 1H, H-7), 3.69 (s, 3H, $CH_3O$—), 2.47 (dd, J=15.7, 7.7 Hz, 1H, H-2), 2.37 (dd, J=15.7 5.8 Hz, 1H, H-2), 2.19 (m, 2H, H-21), 2.14 (m, 2H, H-22), 2.13 (m, 2H, H-16), 2.00 (m, 1H, H-8), 1.98 (m, 1H, H-9), 1.94 (m, 1H, H-5eq), 1.92 (m, 1H, H4eq), 1.80 (m, 1H-8), 1.65 (m, 1H, H-5ax), 1.56 (m, 1H, H-11), 1.55 (m, 1H, H-4ax), 1.45 (m, 1H, H-9), 1.38 (m, 1H, H-12), 1.37 (m, 1H, H-11), 1.28 (m, 1H, H-12), 1.30-1.20 (m, 6H, H-13, H-14 and H-15); $^{13}$C NMR ($CDCL_3$) 170.4 (s, C-1), 138.2 (d, C-23),133.5 (d, C-20),130.4 (d, C-17),128.5 (d, C-18), 126.0 (d, C-19), 114.8 (t, C-24), 83.7 (d, C-6), 79.9 (d, C-10), 78.5 (d, C-7), 77.8 (d, C-3), 51.9 (q, $CH_3O$—), 38.4 (t, C-2), 35.6 (t, C-11), 33.6 (t, C-22), 32.2 (t, C-21), 31.6 (t, C-9), 29.6 (t, C-13)*, 29.5 (t, C-14)*, 29.2 (t, C-15)*, 28.9 (t, C-4), 28.0 (t, C-8), 27.7 (t, C-16), 26.1 (t, C-12), 25.7 (t, C-5).

The spectroscopic data of the mixture of stolonoxides A (1) and B (2), in particular the IR absorptions at 3460 cm$^{-1}$ and 1745 cm$^{-1}$ and the $^{13}$C NMR singlet at δ 175.1 suggested the presence of two isomeric carboxylic acids. Furthermore, the duplication observed in the $^{13}$C NMR spectrum of the signals attributable to four olefinic methines and two allylic methylenes, with a relative intensity of 9:1, indicated that compounds 1 and 2 only differed in their olefinic pattern. Treatment of this mixture with diazomethane afforded the methyl esters 1b and 2b, that could be isolated after repeated HPLC separations.

The FAB high resolution mass measurement indicated that the major methyl ester 1b had the molecular formula $C_{15}H_{40}O_5$ which implies six degrees of unsaturation. The presence of the methyl ester group was confirmed by the $^1$H NMR singlet at δ 3.69 (s, 3H) and the $^{13}$C NMR signals at 170.4 (s) and 51.9 (q). The $^{13}$C NMR spectrum contained six olefinic carbon signals at δ 138.2 (d), 132.4 (d), 130.8 (d), 124.0 (d), 123.4 (d), and 114.7 (t) attributable to a mono-substituted and two disubstituted double bonds. Furthermore, four doublets of methine carbons bearing oxygen at δ 83.8 (d), 79.9 (d), 78.5 (d), and 77.6 (d) together with the absence of further carbonyl, methine, or quaternary carbon signals in the $^{13}$C NMR spectrum, indicated that 1b was the methyl ester of a $C_{24}$ acid containing three double bonds and two oxygenated rings, which gave rise to the four methines bearing oxygen, and accounted for the remaining two degrees of unsaturation.

The absolute stereochemistry of stolonoxide A (1) has been suggested as 3S, 6S, 7S, 10R by application of the Mosher's method to the C-3, C-6 diol obtained through peroxide ring opening by catalytic hydrogenation. To avoid the apparently confusing results arising from the double MTPA esters we employed the Mosher's chiral auxiliary but on the monohydroxy derivative. This work unambiguously confirms an absolute stereochemistry 3S, 6S, 7S, 1OR for stolonoxide A (1).

The minor methyl ester 2b, obtained by methylation of the natural mixture of 1 and 2, was isolated as a colorless oil of molecular formula $C_{25}H_{40}O$, as indicated by the high resolution mass measurement. A general inspection of the $^1$H and $^{13}$C NMR of both isomers 1b and 2b, clearly stated that their structures were closely related and that they shared the same carbon skeleton and functionalities. However slight differences were observed in the signals corresponding to the conjugated disubstituted double bonds. Thus, the $^{13}$C NMR spectrum exhibited the signals of the olefinic carbons at δ 130.5 (d), 128.4 (d), 126.1 (d), and 133.5 (d) which in the HMQC spectrum were correlated with the proton signals at δ 5.31 (1H, dt, J=11.0 and 7.6 Hz), 5.94 (1H, t, J=11.0 Hz), 6.32 (1H, dd, J=15.1 and 11.0 Hz), and 5.65 (1H, dt, J=15.1 and 6.7 Hz), respectively. The coupling constants observed are consistent with a different geometry for each of the two conjugated double bonds. Since the trains double bond proton signal at δ 5.65 was correlated in the COSY spectrum with an allylic methylene proton signal at δ 2.20 (2H, m) which was in turn coupled with the signal at 8 2.17 (2H, m) due to the methylene allylic to the terminal double bond, the trans double bond must be located at C-19, C-20. The $^{13}$C NMR chemical shifts of the allylic methylene carbons C-21 and C-16 at δ 32.2 (t) and 27.7 (t), respectively, provided confirmation to the proposed oometry for the C-17, C-18 and C-19, C-20 double bonds. It was characterized the structure of the methyl ester as 2b and therefore structure 2 was proposed for stolonoxide B. In the absence of an independent determination of the absolute stereochemistry of 2 it was assumed on biogenetic grounds an identical configuration of the stereogenic centers C-3, C-6, C-7, and C-10 as that determined for stolonoxide A (1).

It is worth noting that the structure determination of esters 1b and 2b aided assignation of the NMR data of the natural mixture of stolonoxides A (1) and B (2) to each of the individual compounds.

Careful separation on reversed phase HPLC allowed isolation of a mixture of the sodium carboxylate salts 1a and 2a. The inspection of the $^1$H and $^{13}$C NMR spectra of 1a and 2a, although clearly indicated that their structures were closely related to those of stolonoxides A (1) and B (2), showed some diagnostic differences. Thus, in the $^{13}$C NMR spectrum the resonances attributed to C-1, to the C-2 methylene, and to the C-3 peroxide methine at δ 177.1 (s), 41.3 (t) and 79.2 (d), respectively, were downfield shifted with respect to the resonances observed in compounds 1 and 2. On the other hand, in the $^1$H NMR spectrum the signals of the methylene protons H-2 and of the methane proton H-3 at δ 2.26 (2H, m) and 4.45 (1H, m), respectively, were upfield shifted with respect to those observed in 1 and 2. These effects can be explained by the presence in 1a and 2a of a carboxylate group at C-1 instead of the corresponding carboxylic group, see Kalinowski H. O.; Berger, S.; Braun, S. *Carbo-13 NMR Spectroscopy* John Wiley and Sons, New York, 1988, pp. 198–213, in agreement with the absorption at 1579 cm$^{-1}$ in the IR spectrum. Treatment of the mixture with HCl and, subsequently, with diazomethane afforded a mixture of the methyl esters 1b and 2b indicating that 1a and 2a were carboxylate salts of 1 and 2, respectively. As the ESIMS of the mixture 1a and 2a displayed an [M−Na]$^-$ ion at m/z 405 in the negative mode and the [M+H]$^+$ and [M+Na]$^+$ ions at a m/z 429 and 451 in the positive mode, it was concluded that the compounds 1b and 2b isolated from *S. socialis* were the corresponding sodium carboxylate salts of the stolonoxidc A (1) and B (2).

The most polar component of the constituents of *S. socialis* was a minor 6:4 mixture of stolonoxide C and D isolated as their corresponding sodium salts (3 and 4). The IR absorption of 3 and 4 at 1584 cm$^{-1}$, characteristic of a carboxylate salt, together with the $^1$H and $^{13}$C NMR spectra suggested that the constituents had to be quite similar to those present in the mixture of stolonoxides A and B sodium carboxylates (1a and 2a). The ESIMS ion [M+H]+ in the positive mode at m/z 429 were consistent with a molecular formula $C_{24}H_{37}O_5Na$. Treatment of the mixture of 3 and 4 with HCl and subsequently with diazomethane afforded the corresponding methyl esters 3b and 4b that unfortunately could not be separated by HPLC under different conditions. However the structure of the methyl esters could be deduced by the spectroscopic study of the mixture. Thus, the molecular formula $C_{25}H_{37}O_5$, obtained from the high resolution mass measurement, indicated that the methyl esters 3b and 4b were isomers of the stolonoxides A and B methyl esters (1b, 2b). Furthermore, the comparison of the $^1H$ and $^{13}C$ NMR spectra indicated that they shared an identical plane structure and that the structural differences had to be due to a different stereochemistry.

The relative stereochemistry at the stereogenic centers C-3, C-6, C-7, and C-10 was established as follows. The axial orientation of H-3 was deduced upon observation of a coupling constant of 11.0 Hz between H-3 and H4ax signals and by the correlations exhibited in the ROESY spectrum between the H-3 signal with the H4eq and H-5ax signals whilst the axial orientation of H-6 was clear from the observation of a coupling constant of 10.9 Hz between H-5ax and H-6 signals and by the cross peaks observed in the ROESY spectrum between the H-6 signals and the H-5eq and H-$^4$ax signals. Furthermore, the analysis of the correlations observed in the ROESY spectrum of the H-7 and H-10 signals with those of the methylene protons at C-8 and C-9 clearly required H-7 and H-10 to be oriented towards opposite sides of the tetrahydrofuran ring. However, the stereochemical relationship between both oxygenated rings could not be unequivocally established by NMR study of the methyl esters 3b and 4b. This stereochemical assignment was deduced by a careful study of the unseparable mixture of epoxides 6 and 7 arising by treatment of the mixture of the methyl esters 3b and 4b with NaOH and subsequently with diazoniethane. Basically the $^1H$ and $^{13}C$ NMR spectra of 6 and 7 were quite similar to those of the epoxide 5 discussed above excepting for the $^1H$ NMR signal of the H-6 at δ 3.79 (1H, m) and the $^{13}C$ NMR doublet of C-6 at δ 71.3. These chemical shifts fit better for an erythro orientation of the substituents around C-6 and C-7 stereogenic centers rather than the alternative threo orientation present in epoxide 5, see Alai, F. Q.; Liu, X. X.; McLaughlin, J. L. J. Nat. Prod. 1999, 62, 504–540. Based in this result it was proposed the relative stereochemistry 3S*, 6S*, 7R*, 10S* for the stolonoxides C and D sodium salts (3a and 4a).

The invention claimed is:

1. A method of treating a mammal affected by cancer, the method comprising administering to the affected mammal a therapeutically effective amount of a stolonoxide compound or a pharmaceutically acceptable composition thereof, the compound having a formula (I):

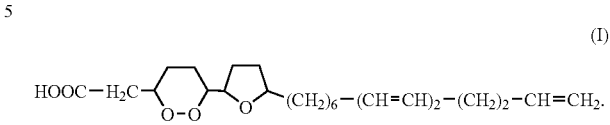

or a pharmaceutically acceptable salt, ester, or amide derivative of the compound.

2. The method of claim 1, wherein the compound is selected from:

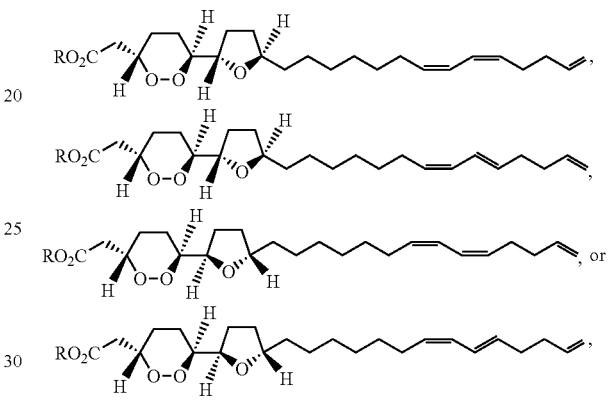

wherein R is H, or a pharmaceutically acceptable salt, ester, or amide derivative of the compound.

3. The method of claim 1, wherein the mammal is a human.

4. A stolonoxide compound, wherein the compound is:

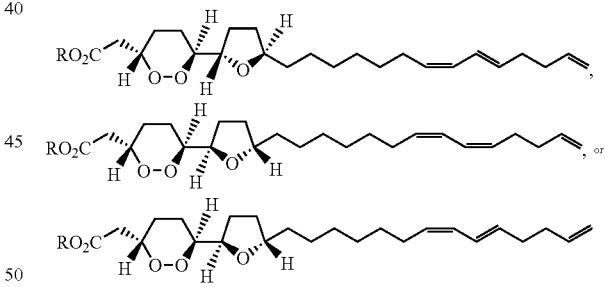

wherein R is H, or a pharmacuetically acceptable salt, ester, or amide derivative of the compound.

* * * * *